US008895260B2

(12) United States Patent
Boettger et al.

(10) Patent No.: US 8,895,260 B2
(45) Date of Patent: Nov. 25, 2014

(54) SCREENING ASSAY FOR RIBOSOMAL ANTIBIOTICS

(75) Inventors: Erik Boettger, Zürich (CH); Andrea Vasella, Zürich (CH); Sven N. Hobbie, Zürich (CH)

(73) Assignee: Eidgenoessicsche Technische Hochschule Zurich eth Transfer, Zurick (CH)

( * ) Notice: Subject to any disclaimer, the term of this patent is extended or adjusted under 35 U.S.C. 154(b) by 1271 days.

(21) Appl. No.: 12/225,706

(22) PCT Filed: Mar. 30, 2007

(86) PCT No.: PCT/EP2007/002861
§ 371 (c)(1),
(2), (4) Date: Oct. 29, 2008

(87) PCT Pub. No.: WO2007/112965
PCT Pub. Date: Oct. 11, 2007

(65) Prior Publication Data
US 2009/0170150 A1    Jul. 2, 2009

(30) Foreign Application Priority Data
Mar. 31, 2006   (EP) .................................. 06006821

(51) Int. Cl.
*C12Q 1/18*   (2006.01)
*C12Q 1/00*   (2006.01)
*C12N 1/20*   (2006.01)

(52) U.S. Cl.
CPC .. *C12N 1/20* (2013.01); *C12Q 1/18* (2013.01); *G01N 2333/35* (2013.01)
USPC ................................................ 435/32; 435/4

(58) Field of Classification Search
USPC ..................................................... 435/32, 4
See application file for complete search history.

(56) References Cited

PUBLICATIONS

Bottger et al. (Structural basis for selectivity and toxicity of ribosomal antibiotics. EMBO reports 2001 2(4) 318-323.*
Thompson et al. (Replacement of the L11 binding region within *E. coli* 23S ribosomal RNA with its homologue from yeast: in vivo and in vitro analysis of hybrid ribosomes altered in the GTPase centre. EMBO 1993 12(4) 1499-1504).*
Jamie J. Cannone, et al., "The Comparative RNA Web (CRW) Site: an online database of comparative sequence and structure information for ribosomal, intron, and other RNAs", BMC Bioinformatics, 2002, vol. 3, No. 2, pp. 1-31.
Robin R. Gutell, et al., "Lessons from an Evolving rRNA: 16S and 23S rRNA Sturctures for a Comparative Perspective", Microbiological Reviews, vol. 58, No. 1, 1994, pp. 10-26.
http:www.hgvs.org; Human Genome Variation Society. Nomenclature for the description of sequence variants (http:www.hgvs.org/mutnomen); Recommendations for the description of RNA sequence variants (www.hgvs.org/mutnomen/recs-RNA.html) Total of 7 pages.

* cited by examiner

*Primary Examiner* — Karen Cochrane Carlson
*Assistant Examiner* — Natalie Mosss
(74) *Attorney, Agent, or Firm* — Nath, Goldberg & Meyer; Joshua B. Goldberg; Tanya E. Harkins

(57) ABSTRACT

The present invention is directed to a method for identifying ribosomal antimicrobial substances being selective for microbial but not for mitochondrial and/or cytosolic ribosomes. Specifically, said method is directed to an assay that compares the interaction of a candidate ribosomal antimicrobial substance (i) in a bacterial strain with microbial ribosomes, and (ii) in a bacterial strain with chimeric mitochondrial bacterial ribosomes, and/or (iii) in a bacterial strain with chimeric cytosolic bacterial ribosomes. In a further aspect the present invention also relates to the use of bacterial strains with microbial ribosomes, and bacterial strains with chimeric mitochondrial bacterial ribosomes, and/or bacterial strains with chimeric cytosolic bacterial ribosomes for identifying ribosomal antimicrobial substance being selective for microbial but not for mitochondrial and/or cytosolic ribosomes. Furthermore, one or more of the above bacterial strains (i) to (iii) may be substituted by a functionally equivalent cell-free biological system.

11 Claims, 2 Drawing Sheets

SCREENING ASSAY FOR RIBOSOMAL ANTIBIOTICS

The present invention is directed to a method for identifying ribosomal antimicrobial substances being selective for microbial but not for mitochondrial and/or cytosolic ribosomes. Specifically, said method is directed to an assay that compares the interaction of a candidate ribosomal antimicrobial substance (i) in a bacterial strain with microbial ribosomes, and (ii) in a bacterial strain with chimeric mitochondrial bacterial ribosomes, and/or (iii) in a bacterial strain with chimeric cytosolic bacterial ribosomes. In a further aspect the present invention also relates to the use of bacterial strains with microbial ribosomes, and bacterial strains with chimeric mitochondrial bacterial ribosomes, and/or bacterial strains with chimeric cytosolic bacterial ribosomes for identifying ribosomal antimicrobial substance being selective for microbial but not for mitochondrial and/or cytosolic ribosomes. Furthermore, one or more of the above bacterial strains (i) to (iii) may be substituted by a functionally equivalent cell-free biological system.

BACKGROUND OF THE INVENTION

The present invention relates to the field of ribosomal antimicrobial substances. The microbial ribosome is the target for many important antimicrobial substances, e.g. antibiotics. These compounds interfere with essential steps of protein synthesis. Ribosomal antimicrobial substances interfere with the microrganism's protein synthesis in such a manner that its propagation is reduced or it is killed. Today, the term antimicrobial substance is understood to encompass all substances that are active against microorganisms of any origin such as bacteria, protozoa and fungi. Ribosomal antimicrobial substances, in particular ribosomal antibiotics comprise, for example, 2-deoxystreptamine aminoglycosides, compounds of the streptomycin family, macrolides, lincosamides and streptogramin B.

Microbial resistance is a common problem with antimicrobial therapy these days. Recent reports indicate that resistance may be the result of one or more mutation(s) within the ribosomal RNA. The investigation of these mutations has proven difficult because microorganisms, e.g. bacteria, generally have several gene copies of rDNA per genome. However, new mutational strategies employing bacteria with low rRNA operon copy numbers such as *Mycobacterium smegmatis* allow for the study of the molecular basis of antimicrobial substance resistance. (Sander et al. Introducing mutations into a chromosomal rRNA gene using a genetically modified eubacterial host with a single rRNA operon, Molecular Microbiology (1996) 22(5), 841-848).

For example, the following positions were identified to confer resistance to antimicrobial substances, e.g. antibiotics: 1408 (Sander, supra), and 1491 (Pfister at al. Mutagenesis of 16 S rRNA C1409-G1491 base-pair differentiates between 6'OH and 6'NH$_3^+$ aminoglycosides, J. Mol. Biol. (2005) 346: 467-475)) in 16sRNA and position 2058 in 23 S rRNA (Sander et al. Mol. Microbiol. 1997, 26: 469-484). Specifically, the mutations A1408G, G1491C(A) and A2058G confer resistance depending on the antimicrobial substance employed. All reference numbers indicating nucleotide positions are based on the numbering of *E. coli*.

The corresponding positions in eukaryotic cytosolic rRNA are 1408G, 1491A, and 2058G, while the same position in eukaryotic mitochondrial rRNA are 1408A, 1491C, and 2058G.

From the above it becomes evident, that cytosolic and mitochondrial ribosomes may be susceptible or resistant to antimicrobial activity depending on the drug and the rRNA composition.

It has been suggested (Böttger et al., Structural basis for selectivity and toxicity of ribosomal antibiotics, EMBO reports, (2001) Vol. 2:4, 318-323) that "The in vitro and in vivo selection of drug resistant bacteria, mapping of resistance conferring mutations and comparison to eukaryotic (mitochondrial and cytoplasmic) ribosomal nucleic acid and protein sequences may offer an important strategy to predict the specificity and toxicity of future antibiotics targeting the bacterial ribosome."

At present, antimicrobial substances, in particular antibiotics are tested for antimicrobial activity and resistance by contacting microorganisms directly whereas toxicity is tested by contacting eukaryotic cells and animals.

It is the object of the present invention to provide a faster, more economical, and simpler method for determining the specificity and toxicity of candidate antimicrobial substances. This object is solved by providing a method for identifying ribosomal antimicrobial substances being selective for microbial but not for mitochondrial and/or cytosolic ribosomes, comprising the following steps:

a) providing
   (i) at least one bacterial strain with microbial ribosomes, and
   (ii) at least one bacterial strain with chimeric mitochondrial bacterial ribosomes, and/or
   (iii) at least one bacterial strain with chimeric cytosolic bacterial ribosomes;
b) contacting a candidate ribosomal antimicrobial substance with each of the bacterial strains according to a);
c) determining an interaction of the candidate ribosomal antimicrobial substance with one or more of the ribosomes of each of the bacterial strains according to a).

It was found that microbial systems comprising (i) microbial, preferably bacterial, (ii) chimeric mitochondrial bacterial and/or (iii) chimeric cytosolic bacterial ribosomes are sufficient for determining the ribosomal specificity and, consequently, the toxicity of ribosomal antimicrobial substances. The method of the present invention relies completely on bacterial cells and avoids the eukaryotic cell systems and animal models that were employed until now for specificity and toxicity testing. Bacterial systems are much more economical from a point of costs, replication time, manipulation and handling than their eukaryotic counterparts. It was demonstrated that the results obtained with purely bacterial strains significantly coincide with the results obtained with eukaryotic cell systems and animals.

In a preferred embodiment of the method of the present invention at least one of the bacterial strains mentioned in sections (i) to (iii) above may be substituted by a functionally equivalent cell-free biological system. More preferably, at least two, most preferably all three bacterial strains mentioned in sections (i) to (iii) above are substituted by a functionally equivalent cell-free biological system. In this respect it is to be noted that the term "bacterial strain" is meant to encompass functionally equivalent cell-free biological systems. The term "cell-free system" is well understood by those skilled in the art and does not require any further comment. Also, methods for providing cell-free systems are common general knowledge in the art and are routinely practiced by those of average skill in the art. The term "functionally equivalent" in the above respect is meant to relate to cell-free systems that comprise at least a functional ribosomal system capable of translational activity for producing polypeptides from nucleotides.

The term "ribosomal antimicrobial substance" is meant to define compounds that specifically interact with microbial, preferably bacterial ribosomes and function as antimicrobial, preferably bacteriocidal and/or bacteriostatic agents.

Ribosomal antimicrobial substances selective for microbial, preferably bacterial ribosomes, according to the present invention are those that do not affect mitochondrial and/or cytosolic ribosomes, preferably those that do not affect mitochondrial and cytosolic ribosomes.

The term "microbial ribosome" includes wild-type and chimeric ribosomes of micro-organisms, such as fungal, bacterial and protozoic ribosomes.

Antibiotics have been shown to be effective ribosomal antimicrobial substances in various microbial organisms such as, e.g. the helminth *Echinococcus multicularis* (Mathis et al. Antimicrobial Agents and Chemotherapy, August 2005: 3251-3255) and the protozoan *Acanthamoeba castellanii* (Mathis et al. Molecular & Biochemical Parasitology, 135, 223-227, 2004). Hence, the method of the invention is suitable for identifying ribosomal antimicrobial substances, in particular antibiotics, selective for many, most or even all types of microbial organisms. For example, the method of the present invention is suitable for identifying antimicrobial substances that are selective for the parasites giving rise to leishmaniasis and trypanosomiasis.

The term "chimeric mitochondrial bacterial ribosome" and the term "chimeric cytosolic bacterial ribosome" are meant to define a ribosome which is derived from a bacterial ribosome, wherein one or more nucleotide(s) of the ribosomal RNA has/have been replaced by the corresponding nucleotide from a mitochondrial ribosome or a cytosolic ribosome, respectively.

Typically, the contacting in step b) of the method of the present invention is effected by adding at least one candidate antimicrobial substance, optionally in a solvent or solvent system, to the bacteria or the functionally equivalent cell-free biological system directly, e.g. placing it onto the surface of the bacteria or cell-free system, or indirectly, e.g. adding the antimicrobial substance to the liquid or solid medium (e.g. gel, beads) surrounding or underlying the bacterial strain(s) or cell-free system(s). The contacting step is non-limiting and may be effected in any suitable manner known to the person skilled in the art.

The selectivity of the candidate antimicrobial substance and, consequently, the toxicity with regard to mitochondrial or cytosolic ribosomes may be determined by routine methods, in particular by comparing the candidate antimicrobial substance' inhibitory activity on the growth of bacterial strains and/or functionally equivalent cell-free ribosomal biological systems comprising (i) microbial ribosomes, and (ii) chimeric mitochondrial bacterial ribosomes, and/or (iii) chimeric cytosolic bacterial ribosomes.

In a preferred embodiment the method of the invention is one for identifying ribosomal antimicrobial substances selective for bacterial, protozoic and/or fungal ribosomes, preferably selective for bacterial and/or protozoic ribosomes, more preferably selective for bacterial ribosomes. In a particularly preferred embodiment, the method of the present invention is suitable for identifying antimicrobial substances selective for the protozoa giving rise to leishmaniasis and/or trypanosomiasis.

In a more preferred embodiment of the method of the invention the at least one bacterial strain (or functionally equivalent cell-free system) with microbial ribosomes of step a) (i) comprises microbial ribosomes selected from the group consisting of natural or chimeric bacterial, protozoic and fungal ribosomes, preferably natural or chimeric bacterial and/or protozoic ribosomes, more preferably natural or chimeric bacterial ribosomes. The bacterial strain (or functionally equivalent cell-free system) comprises at least one of said microbial ribosomes and may comprise microbial ribosomes of more than one microorganism, e.g. fungal and bacterial, fungal and protozoic, protozoic and bacterial or protozoic, fungal and bacterial ribosomes.

Preferred candidate ribosomal antimicrobial substances are selected from the group consisting of aminoglycosides, macrolides, lincosamides, preferably aminoglycosides, more preferably 2-deoxystreptamines.

Although the microbial ribosomes may be any bacterial ribosomes when antimicrobial substances selective against bacteria, i.e. antibiotics, are desired, it is preferred that the microbial ribosomes for use in the method of the invention are bacterial ribosomes from *Mycobacterium smegmatis*.

For identifying ribosomal antimicrobial substances selective against fungi it is preferred that the microbial ribosomes are chimeric fungal ribosomes characterized in that they are derived from bacterial ribosomes comprising at least one mutation selected from the group consisting of 1408A, 1410G, 1490C, and 1491G of according to the numbering of *E. coli*.

For identifying ribosomal antimicrobial substances selective against protozoa it is preferred that the microbial ribosomes are chimeric protozoic ribosomes characterized in that they are derived from bacterial ribosomes comprising at least one mutation selected from the group consisting of 1408A, 1409U, 1409A, 1410G, 1410 A, 1490U, 1491G, 1491U and 2058A of according to the numbering of *E. coli*.

Preferred chimeric mitochondrial bacterial ribosomes for practicing the method of the present invention are characterized in that they are derived from bacterial ribosomes comprising at least the mutation of G1491C according to the numbering of *E. coli*, preferably having further mutations selected from the group consisting of G1410C, U1411C, C1412U, A1413C, U1414C, G1415U, A1416C, U1484G, U1485A, G1488A, A1489G and C1490A.

More preferably, the chimeric mitochondrial bacterial ribosomes comprise mutations G1410C, U1411C, C1412U, A1413C, U1414C, G1415U, A1416C, U1484G, U1485A, G1488A, A1489G and C1490A.

Most preferably, the chimeric mitochondrial bacterial ribosomes are further humanized by mutation(s), preferably by mutation(s) in the ribosomal decoding site.

Preferred chimeric cytosolic bacterial ribosomes for practicing the method of the present invention are characterized in that they are derived from bacterial ribosomes comprising at least the mutation(s) of A1408G and/or G1491A according to the numbering of *E. coli*, more preferably having further mutations selected from the group consisting of G1410U, U1411A, A1413U, U1414A, G1415C, A1416C, U1484G, U1485G, G1486A, G1487A, A1489U, and C1490A.

More preferably, the chimeric cytosolic bacterial ribosomes comprise mutations G1410U, U1411A, A1413U, U1414A, G1415C, A1416C, U1484G, U1485G, G1486A, G1487A, A1489U, and C1490A, and much more preferably further comprise A1408G and G1491A.

Most preferably, the chimeric cytosolic bacterial ribosomes are further humanized by mutation(s), preferably in the ribosomal decoding site.

It is noted that the method of the invention is not limited to microbial ribosomes featuring mutations in the 16S rRNA much less is it limited to mutations in the decoding site of 16S rRNA. The embodiments herein relating to mutations in the decoding site of 16S rRNA merely serve as examples for illustrating the present invention and are by no means meant to limit its scope. For example, the method of the present invention encompasses any manipulations of functionally relevant regions of 16S rRNA or 23S rRNA that have a natural sequence polymorphism that can serve as a mutational basis for the method of the invention.

While there are a number of standard methods for determining the interaction of ribosomal antimicrobial substances available to those skilled in the art, it is preferred that for practicing the method of the invention the interaction of the ribosomal antimicrobial substance is determined by calculating the minimal inhibitory concentration (MIC) of the antimicrobial substance in each of the bacterial strains and/or cell-free systems according to step a), preferably the MIC of the antimicrobial substance relative to the MIC of the bacterial strain and/or cell-free system (i).

In a preferred embodiment the candidate antimicrobial substance identified according to the present invention is selective for bacterial, fungal and/or protozoic but not for mitochondrial and cytosolic ribosomes. More preferred it is selective for bacterial ribosomes, i.e. a ribosomal antibiotic.

In order to avoid interference of the bacterial cell's (or cell-free system's) own naturally occurring ribosomes with the introduced at least partially heterologous, mitochondrial or cytosolic bacterial ribosomes, at least part of at least one gene encoding the naturally occurring ribosomes can be modified, replaced or deleted.

In a preferred embodiment the method according to the invention is one, wherein the
 (i) at least one bacterial strain with microbial ribosomes, and/or
 (ii) at least one bacterial strain with chimeric mitochondrial bacterial ribosomes, and/or
 (iii) at least one bacterial strain with chimeric cytosolic bacterial ribosomes;
is a bacterial strain, wherein at least part of at least one gene encoding the naturally occurring bacterial ribosomal RNA sequence has been deleted and replaced by at least part of at least one gene encoding a heterologous microbial (i), mitochondrial (ii) and/or cytosolic (iii) ribosomal RNA sequence, respectively. Again, instead of said bacterial strains equivalent cell-free biological systems can be employed.

More preferably, the bacterial strain for practicing the method is *Mycobacterium smegmatis*, wherein at least part of the rrnA and/or rrnB gene(s) has (have) been deleted and replaced by at least part of at least one gene encoding a heterologous microbial (i), mitochondrial (ii) and/or cytosolic (iii) ribosomal RNA sequence.

In another preferred embodiment the cell-free system for practicing the invention is a system comprising bacterial ribosomal components, preferably from *Mycobacterium smegmatis*, preferably comprising its ribosome(s), wherein at least part of the chromosomal rRNA, preferably rrnA and/or rrnB gene(s), has (have) been deleted and replaced by at least part of at least one gene encoding a heterologous microbial (i), mitochondrial (ii) and/or cytosolic (iii) ribosomal RNA sequence.

Another aspect of the present invention relates to the use of bacterial strains or functionally equivalent cell-free biological systems in a method according to the invention.

In a preferred embodiment of this aspect, the invention relates to the use of bacterial strains or functionally equivalent cell-free biological systems comprising chimeric fungal ribosomes characterized in that they are derived from bacterial ribosomes, wherein the ribosomes are characterized in that they are derived from bacterial ribosomes comprising at least one mutation selected from the group consisting of 1408A, 1410G, 1490C, and 1491G of according to the numbering of *E. coli* in a method according to the invention.

In another preferred embodiment of this aspect, the invention relates to the use of bacterial strains or functionally equivalent cell-free biological systems comprising chimeric protozoic ribosomes characterized in that they are derived from bacterial ribosomes, wherein the ribosomes are characterized in that they are derived from bacterial ribosomes comprising at least one mutation selected from the group consisting of 1408A, 1409U, 1409A, 1410G, 1410 A, 1490U, 1491G, 1491U and 2058A of according to the numbering of *E. coli* in a method according to the invention.

In another preferred embodiment of this aspect, the invention relates to the use of bacterial strains or functionally equivalent cell-free biological systems comprising chimeric mitochondrial bacterial ribosomes characterized in that they are derived from bacterial ribosomes comprising at least the mutation of G1491C according to the numbering of *E. coli*, preferably having further mutations selected from the group consisting of G1410C, U1411C, C1412U, A1413C, U1414C, G1415U, A1416C, U1484G, U1485A, G1488A, A1489G and C1490A in a method according to the invention.

More preferably, the chimeric mitochondrial bacterial ribosomes comprise mutations G1410C, U1411C, C1412U, A1413C, U1414C, G1415U, A1416C, U1484G, U1485A, G1488A, A1489G and C1490A.

Most preferably, the chimeric mitochondrial bacterial ribosomes are further humanized by mutation(s), preferably in the ribosomal decoding site.

In a further preferred embodiment of this aspect, the invention relates to the use of bacterial strains or functionally equivalent cell-free biological systems comprising chimeric cytosolic bacterial ribosomes characterized in that they are derived from bacterial ribosomes comprising at least the mutation of A1408G and/or G1491A according to the numbering of *E. coli*, more preferably having further mutations selected from the group consisting of G1410U, U1411A, A1413U, U1414A, G1415C, A1416C, U1484G, U1485G, G1486A, G1487A, A1489U, and C1490A in a method according to the invention.

More preferably, the chimeric cytosolic bacterial ribosomes comprise mutations G1410U, U1411A, A1413U, U1414A, G1415C, A1416C, U1484G, U1485G, G1486A, G1487A, A1489U, and C1490A, and more preferably further comprise mutations A1408G and G1491A.

Most preferably, the chimeric cytosolic bacterial ribosomes are further humanized by mutation(s), preferably in the ribosomal decoding site.

As mentioned before, in order to avoid interference of the bacterial cell's (or cell-free biological system's) own naturally occurring ribosomes with the introduced at least partially heterologous, mitochondrial or cytosolic bacterial ribosomes, at least part of at least one gene encoding the naturally occurring ribosomes can be modified, replaced or deleted.

Therefore, in another preferred embodiment the present invention relates to the use of a bacterial strain or functionally equivalent cell-free biological system, wherein at least part of at least one gene encoding the naturally occurring bacterial ribosomal RNA sequence has been deleted and replaced by at least part of at least one gene encoding a heterologous microbial (i), mitochondrial (ii) and/or cytosolic (iii) ribosomal RNA sequence in a method according to the invention.

More preferably, the present invention is directed to the use according to the invention, wherein the bacterial strain is *Mycobacterium smegmatis* or wherein the functionally equivalent cell-free biological system is derived from *Mycobacterium smegmatis*, wherein at least part of the rrnA and/or rrnB gene(s) has (have) been deleted and replaced by at least part of at least one gene encoding a heterologous microbial (i), mitochondrial (ii) and/or cytosolic (iii) ribosomal RNA sequence.

A further aspect of the present invention relates to a kit of parts comprising any one or more of the above bacterial strains or functionally equivalent cell-free biological systems or components thereof for use in the method of the present invention and optionally written instructions, buffer materials, bacterial nutrient(s), aqueous solvent(s), antimicrobial substance(s), etc.

In the following specific embodiments of the present invention will be described for the purpose of illustrating the present invention and for providing a best mode for carrying out the invention.

EXAMPLES

Example 1

Figure 1:
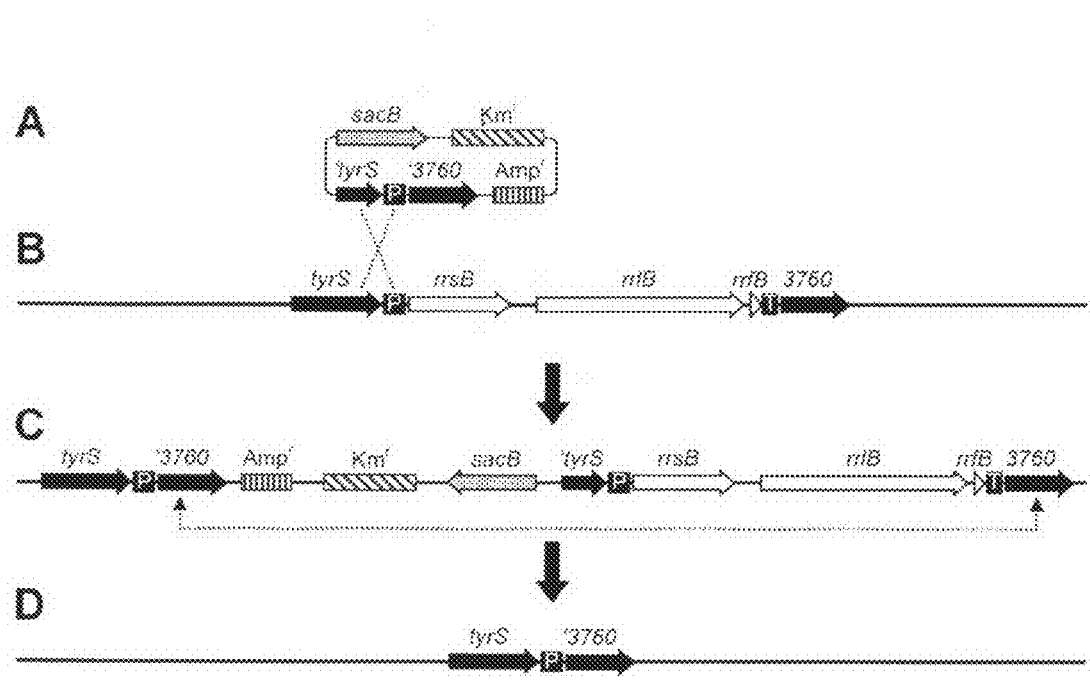
FIG. 1: illustrates the strategy for deletion of rRNA operon rrnB according to example 3. Open arrows represent rRNA genes; P and T the promoter and termination sequences, respectively. Solid arrows indicate the open reading frames upstream and downstream of rrnB. Hatched rectangles represent antibiotic resistance cassettes, the stippled arrow the sacB gene. Broken lines indicate possible crossover sites between homologous sequences in the replacement vector (A) and the chromosomal target site (B). Following plasmid integration into the rrnB 5'-flanking region (C), a second crossover event between the homologous 3'-flanking sequences resolves the chromosomal tandem repeat to the deletion of rrnB (D).

General Method for Mutating the rRNA Gene of *M. smegmatis*

Using a genetically modified derivative of *Mycobacterium smegmatis* (Sander et al. Mol. Microbiol. 1996, 22: 841-848) and a plasmid carrying a partial rRNA gene fragment with the desired mutation, this mutation may be subsequently introduced into the single functional chromosomal rRNA operon by RecA homologous recombination (Prammananan et al. Antimicrob. Agents Chemother. 1999, 43: 447-453). For further details see also Pfister et al. ChemBioChem 2003, 4: 1078-1088.

Example 2

Production of Recombinant *M. smegmatis* Strains

The strain used for introduction/selection of mutational alterations was a genetically modified derivative of *Mycobacterium smegmatis* carrying a single functional chromosomal rRNA operon (Sander et al. Mol. Microbiol. 1996, 22: 841-848). This strain, termed *M. smegmatis* rrn⁻, allowed for the selection of mutational alterations in the single copy rRNA gene. Using a plasmid carrying the rRNA gene with the respective mutational alteration, the mutation was subsequently introduced into the single functional rRNA operon by RecA-mediated homologous recombination (Prammananan et al. Antimicrob. Agents Chemother. 1999, 43: 447-453).

The rRNA gene carried on the plasmid encodes either the complete rRNA operon (Prammananan et al. Antimicrob. Agents Chemother. 1999, 43: 447-453) or a non-functional rRNA gene fragment of approximately 1.0 kb (Pfister et al. Antimicrob. Agents Chemother. 2003, 47: 1496-1502). PCR-mutagenesis in vitro was used to generate the mutagenized rRNA gene fragment. In the case of a partial rRNA gene fragment the mutagenized rRNA gene fragment was cloned into vectors pMV261 or pMV361 (Sander et al. Mol. Microbiol. 2002, 46: 1295-1304; Pfister et al. Antimicrob. Agents Chemother. 2003, 47: 1496-1502) to result in vectors carrying a partial rRNA gene fragment of approximately 1.0 kb with the mutational alteration introduced. In the case of plasmids carrying the complete rRNA operon the mutagenized rRNA gene fragment obtained by PCR was cloned into vectors pMV361 rRNA or pMV261 rRNA using appropriate restriction sites (Prammananan et al. Antimicrob. Agents Chemother. 1999, 43: 447-453). Vectors pMV361 rRNA and pMV261 rRNA carried a complete copy of the rRNA operon from *M. smegmatis* (Sander et al., Mol. Microbiol. 1997, 26: 469-480). Introduction of mutations into the plasmid encoded rRNA was confirmed by sequencing.

The single rRNA allelic derivative of *M. smegmatis*, i.e. *M. smegmatis* rrn⁻, was used for transformation of the plasmids. The strain was made electro-competent and transformed according to standard techniques and as described previously (Sander et al. Mol. Microbiol. 1997, 26: 469-484). Following primary selection, the plasmid-encoded mutational rRNA gene alteration was transferred into the single chromosomal rRNA operon by means of RecA-mediated homologous recombination (Prammananan et al. Antimicrob. Agents Chemother. 1999, 43: 447-453). Introduction of the mutational rRNA gene alteration into the single functional chromosomal rRNA operon by gene conversion was confirmed by sequence determination.

In another aspect of the technique, the single functional chromosomal rRNA operon was inactivated and the synthesis of ribosomal RNA was driven exclusively by the mutated plasmid-encoded rRNA operon.

The recombinants carrying the respective mutational alterations in the functional rRNA operon were colony-purified and subjected to determinations of minimal inhibitory concentrations (MIC) to determine ribosomal drug susceptibility. Cultures from single colonies were grown in LB medium supplemented with 0.05% Tween 80 and used for MIC tests in a microtiter plate format. Starting cultures contained 200 μl of bacterial cells at an optical density of 0.025 at 600 nm, and the respective drug was added in twofold series of dilution. The MIC was defined as the drug concentration at which the growth of the cultures was completely inhibited after 72h of incubation at 37° C., corresponding to 24 generations.

Example 3

Production of the Recombinant *M. smegmatis* Strain ΔrrnA ΔrrnB attB::prrnB

The following demonstrates one way of producing a strain with all endogenous rrn genes deleted and with functional ribosomal RNA produced by a plasmid encoded rRNA operon A combination of positive, e.g. aph, and negative-selectable markers, e.g. sacB, was used for unmarked deletion mutagenesis. In brief, the sacB gene was cloned into the mycobacterial expression vector pMV361 (Stover et al. Nature 1991, 351:456-460) to result in pMS32a. In pMS32a, sacB is located downstream of the hsp60 promoter. A restriction fragment of pMS32a carrying the hsp60p-sacB construct was transferred into the cloning vector pGEM-7 (Promega) to result in plasmid pZ130 which was used as backbone in the construction of both rrnA and rrnB replacement vectors. Chromosomal DNA sequences flanking the 5' and 3' region of each rrn operon were obtained by PCR and cloned into pZ130. Following further modifications, the rrn replacement vectors were obtained. As example, the generation of the rrnB replacement vector is described here and the strategy for inactivation of rrnB illustrated in FIG. 1.

Figure 2:
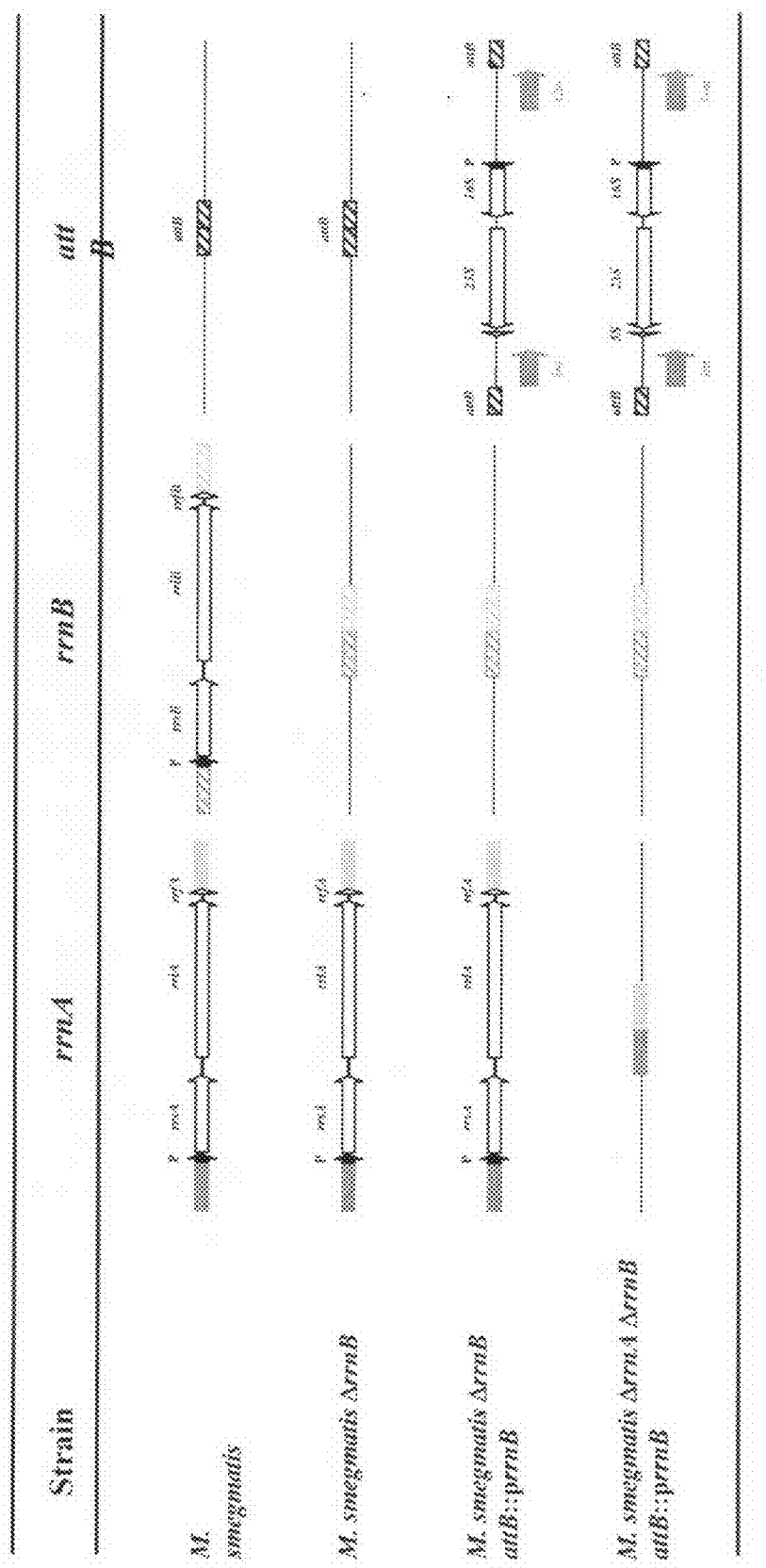
FIG. 2 illustrates the sequential strategy for the generation of *M. smegmatis* ΔrrnA ΔrrnB attB::prrnB according to example 3. Following deletion of chromosomal rrnB, a complementation vector carrying a functional rrnB operon is introduced to the chromosomal attB site. Subsequent deletion of rrnA results in strain *M. smegmatis* ΔrrnA ΔrrnB attB::prrnB, in which ribosomal RNA is exclusively transcribed from the plasmid.

For complementation, a functional rrnB operon was cloned into an integration-proficient vector. Following the strategy outlined in FIG. 2 a derivative of *M. smegmatis*, i.e. strain ΔrrnA ΔrrnB attB::prrnB, was obtained where both endogenous chromosomal rRNA operons are inactivated by gene deletion across the entire 16S, 23S, and 5S rRNA genes (rrs, rrl, and rrf; see FIG. 1). This strain is completely devoid of chromosomal rRNA genes and rRNA is exclusively transcribed from plasmid DNA.

Such strains are particularly useful because they avoid the interference of the bacterial cell's own naturally occurring ribosomal activity with that of the introduced at least partially heterologous, mitochondrial or cytosolic bacterial ribosomes in the assay methods of the present invention.

Example 4

Screening Assay for Ribosomal Antibiotics Using Recombinant *M. smegmatis*

This assay demonstrated that bacterial ribosomes carrying 'human' rRNA nucleotide positions are useful as surrogate to study the interaction of drugs with the human ribosome. This was illustrated by the polymorphism of 16S rRNA position 1408 and susceptibility to 4,6-aminoglycosides with a 6' $NH_3$ group (e.g. gentamicin, tobramycin, kanamycin). 4,6-aminoglycosides with a 6' $NH_3$ group bound to the ribosomal A-site encompassing nucleotides 1400-1900 and selectively targeted the bacterial ribosome, but not the eukaryotic cytoplasmic ribosome. An important polymorphism in the rRNA concerns nucleotide position 1408: prokaryotic ribosomes are characterized by an adenine, eukaryotic cytoplasmic ribosomes by a guanine. Replacing the adenine by a guanine at 16S rRNA position 1408 made the bacterial ribosome completely unsusceptible towards 4,6-amino-glycosides with a 6' $NH_3$ group (see Table). Thus, a single nucleotide alteration which introduces the human nucleotide position 1408 into the bacterial ribosome confered high-level drug resistance similar to the natural drug resistance of eukaryotic cytoplasmic ribosomes.

The data of Table 1 shows (i) that single nucleotide polymorphisms in the rRNA can determine the selectivity and specificity of ribosomal drugs, and ii) that appropriately modified bacterial ribosomes can be constructed and used to study the interaction of drugs with the eukaryotic ribosome.

TABLE 1

Drug susceptibility of rRNA mutants

| | Gentamicin MIC[a] | Tobramycin MIC[a] |
|---|---|---|
| wild type bacterial cells 1408A | 1 | 2 |
| mutant bacterial cells 1408G | >1024 | >1024 |

[a] MIC, minimal inhibitory concentration (μg/ml)

Example 5

Screening Assay for Ribosomal Antibiotics Directed Against a Protozoan rRNA Decoding Site Using Recombinant *M. smegmatis*

The MIC data shown below in example 5 were obtained with bacterial hybrid ribosomes carrying human and protozoan rRNA decoding sites in a method of the invention. The data as well as the secondary structures of human and protozoan rRNA decoding sites demonstrate the utility of the method of the present invention for identifying ribosomal antimicrobial substances directed at a specific protozoan rRNA decoding site (here *Leishmania* and *Trypanosoma* protozoans). Nucleotide positions depicted in bold represent residues that are specific for the corresponding eukaryotic decoding site. The part of the human and protozoan decoding sites introduced into the bacterial ribsosome is boxed. The nucleotide positions are numbered according to the numbering of homologous positions in *E. coli* 16S rRNA.

| | MIC (μ/ml) | |
|---|---|---|
| M. smegmatis | Homo sapiens mitochondrion | Leishmania Trypanosoma |
| (rRNA secondary structure, positions 1400–1490) | (rRNA secondary structure, positions 1400–1490) | (rRNA secondary structure, positions 1400–1490) |
| Paromomycin  1 | >1024 | 128 |
| Neomycin  0.5 | 16-32 | >1024 |
| Tobramycin  1 | 64-128 | 1024 |
| Gentamicin  1 | 64-128 | >1024 |

The invention claimed is:

1. A method for identifying ribosomal antimicrobial substances being selective for microbial but not for mitochondrial and cytosolic ribosomes, comprising the following steps:
   a) providing
      (i) at least one bacterial strain or a functionally equivalent cell-free biological system with microbial ribosomes, and
      (ii) at least one bacterial strain or a functionally equivalent cell-free biological system with chimeric mitochondrial bacterial ribosomes comprising chimeric rRNA, and
      (iii) at least one bacterial strain or a functionally equivalent cell-free biological system with chimeric cytosolic bacterial ribosomes comprising chimeric rRNA;
   b) contacting a candidate ribosomal antimicrobial substance with each of the bacterial strains or a functionally equivalent cell-free biological system according to a);
   c) determining an interaction of the candidate ribosomal antimicrobial substance with one or more of the ribosomes of each of the bacterial strains or a functionally equivalent cell-free biological system according to a); and
   d) identifying the candidate ribosomal antimicrobial substance as being selective for microbial ribosomes and not for mitochondrial ribosomes and cytosolic ribosomes, when said candidate ribosomal antimicrobial substance interacts with microbial ribosomes but does not interact with chimeric mitochondrial bacterial ribosomes and with cytosolic bacterial ribosomes of the bacterial strains of a).

2. The method according to claim 1, wherein the ribosomal antimicrobial substance is selective for bacterial, protozoic and/or fungal ribosomes.

3. The method according to claim 1, wherein the at least one bacterial strain with microbial ribosomes comprises microbial ribosomes selected from the group consisting of natural or chimeric bacterial, protozoic and fungal ribosomes.

4. The method according to claim 1, wherein the candidate ribosomal antimicrobial substance is selected from the group consisting of aminoglycosides, macrolides, lincosamides.

5. The method according to claim 1, wherein the microbial ribosomes are bacterial ribosomes from *Mycobacterium smegmatis*.

6. The method according to claim 1, wherein the interaction of the ribosomal antimicrobial substance is determined by calculating the minimal inhibitory concentration (MIC) of the antimicrobial substance in each of the bacterial strains according to step a).

7. The method according to claim 1, wherein the identified candidate antimicrobial substance is selective for bacterial, fungal and/or protozoic but not for mitochondrial and cytosolic ribosomes.

8. The method according to claim 1, wherein the
   (i) at least one bacterial strain with microbial ribosomes, and/or
   (ii) at least one bacterial strain with chimeric mitochondrial bacterial ribosomes, and/or
   (iii) at least one bacterial strain with chimeric cytosolic bacterial ribosomes;
is a bacterial strain, wherein at least part of at least one gene encoding the naturally occurring bacterial ribosomal RNA sequence has been deleted and replaced by at least part of at least one gene encoding a heterologous microbial (i), mitochondrial (ii) and/or cytosolic (iii) ribosomal RNA sequence, respectively.

9. The method of claim 8, wherein the bacterial strain is *Mycobacterium smegmatis*, wherein at least part of the rrnA and/or rrnB gene(s) has (have) been deleted and replaced by at least part of at least one gene encoding a heterologous microbial (i), mitochondrial (ii) and/or cytosolic (iii) ribosomal RNA sequence.

10. The method according to claim 9, wherein at least one of said bacterial strains is substituted by a functionally equivalent cell-free biological system.

11. The method according to claim 1, wherein the ribosomal antimicrobial substance is selective for ribosomes of *leishmania* or *trypanosomia* protozoans.

\* \* \* \* \*

UNITED STATES PATENT AND TRADEMARK OFFICE
CERTIFICATE OF CORRECTION

PATENT NO.         : 8,895,260 B2
APPLICATION NO.    : 12/225706
DATED              : November 25, 2014
INVENTOR(S)        : Erik Boettger et al.

Page 1 of 1

It is certified that error appears in the above-identified patent and that said Letters Patent is hereby corrected as shown below:

On the Title Page item (73) Assignee: change Eidgenoessische Technische Hochschule Zurich eth Transfer, Zurick (CH) to Eidgenoessische Technische Hochschule Zürich ETH Transfer, Zürich (CH)

Please add second Assignee as:
(73) Assignee: Universität Zürich
Zürich, (CH)

Signed and Sealed this
Second Day of June, 2015

Michelle K. Lee
*Director of the United States Patent and Trademark Office*